(12) United States Patent
Rubin et al.

(10) Patent No.: US 9,678,077 B2
(45) Date of Patent: Jun. 13, 2017

(54) ERG/TFF3/HMWCK TRIPLE IMMUNOSTAIN FOR DETECTION OF PROSTATE CANCER

(71) Applicant: CORNELL UNIVERSITY, Ithaca, NY (US)

(72) Inventors: Mark A. Rubin, New York, NY (US); Juan Miguel Mosquera, New York, NY (US); Kyung Park, Stamford, CT (US); Ya-Lin Chiu, Island Park, NY (US); Francesca Demichelis, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 393 days.

(21) Appl. No.: 14/401,184

(22) PCT Filed: May 15, 2013

(86) PCT No.: PCT/US2013/041155
§ 371 (c)(1),
(2) Date: Nov. 14, 2014

(87) PCT Pub. No.: WO2013/173463
PCT Pub. Date: Nov. 21, 2013

(65) Prior Publication Data
US 2015/0132767 A1    May 14, 2015

Related U.S. Application Data

(60) Provisional application No. 61/647,076, filed on May 15, 2012.

(51) Int. Cl.
| | |
|---|---|
| *G01N 31/00* | (2006.01) |
| *G01N 33/53* | (2006.01) |
| *G01N 33/574* | (2006.01) |
| *C07K 16/18* | (2006.01) |
| *C07K 16/26* | (2006.01) |
| *C07K 16/32* | (2006.01) |

(52) U.S. Cl.
CPC ....... *G01N 33/57434* (2013.01); *C07K 16/18* (2013.01); *C07K 16/26* (2013.01); *C07K 16/32* (2013.01); *G01N 2333/47* (2013.01); *G01N 2333/4742* (2013.01)

(58) Field of Classification Search
None
See application file for complete search history.

(56) References Cited

U.S. PATENT DOCUMENTS

2004/0053334 A1    3/2004    Ratner et al.

FOREIGN PATENT DOCUMENTS

WO    94/01775 A1    1/1994

OTHER PUBLICATIONS

Park et al. (Poster Session VI #169, Mar. 21, 2012, www.uscap.org).*
Berger, M.F. et al., "The genomic complexity of primary human prostate cancer" Nature (Feb. 10, 2011) pp. 214-220, vol. 470, No. 7333.
Demichelis, F. et al., "Distinct Genomic Aberrations Associated with ERG Rearranged Prostate Cancer" Genes, Chromosomes & Cancer (2009) pp. 366-380, vol. 48.
Faith, D.A. et al., "Trefoil Factor 3 Overexpression in Prostatic Carcinoma: Prognostic Importance Using Tissue Microarrays" Prostate (2004) pp. 215-227, vol. 61.
Garaway, I.P. et al., "Trefoil Facotr 3 is Overexpressed in Human Prostate Cancer" Prostate (2004) pp. 209-214, vol. 61.
Jagla, W. et al., "Co-localization of TFF3 peptide and oxytocin in the human hypothalamus" The FASEB Journal (Jun. 2000) pp. 1126-1131, vol. 14.
Kumar-Sinha, C. et al., "Recurrent Gene Fusions in Prostate Cancer" Nat Rev Cancer (Jul. 2008) pp. 497-511, vol. 8, No. 7.
Lapointe, J. et al., "Genomic Profiling Reveals Alternative Genetic Pathways of Prostate Tumorigenesis" Cancer Research (2007) pp. 8504-8510, vol. 67.
Luo, J. et al., "Human Prostate Cancer and Benign Prostatic Hyperplasia: Molecular Dissection by Gene Expression Profiling" Cancer Res (2001) pp. 4683-4688, vol. 61.
Magee, J.A. et al., "Expression Profiling Reveals Hepsin Overexpression in Prostate Cancer" Cancer Res (2001) pp. 5692-5696, vol. 61.
Mosquera, J.M. et al. "Prevalence of TMPRSS2-ERG Fusion Prostate Cancer among Men Undergoing Prostate Biopsy in the United Satates" Clinical Cancer Res (2009) pp. 4706-4711, vol. 15.
Park, K. et al., "Antibody-Based Detection of ERG Rearrangement-Postitive Prostate Cancer" Neoplasia (Jul. 2010) pp. 590-598, vol. 12, No. 7.
Perner, S. et al., "TMPRSS2:ERG Fusion-Associated Deletions Provide Insight into the Heterogeneity of Prostate Cancer" Cancer Res (2006) pp. 8337-8341, vol. 66.
Qian, D.Z. et al., "Prostate cancer—associated gene expression alterations determined from needle biopsies" Clinical Cancer Res (2009) pp. 3135-3142, vol. 15.
Rickman, D.S. et al., "ERG Cooperates with Androgen Receptor in Regulating Trefoil Factor 3 in Prostate Cancer Disease Progression" Neoplasia (Dec. 2010) pp. 1031-1040, vol. 12, No. 12.
Tomlins, S.A. et al., "The Role of SPINK1 in ETS Rearrangement Negative Prostate Cancers" Cancer Cell (Jun. 2008) pp. 519-528, vol. 13, No. 6.
Tomlins, S.A. et al., "ETS Gene Fusions in Prostate Cancer: From Discovery to Daily Clinical Practice" European Urology (2009) pp. 275-286, vol. 56.
Tomlins, S.A. et al., "Recurrent Fusion of TMPRSS2 and ETS Transcription Factor Genes in Prostate Cancer" Science (2005) pp. 644-648, vol. 310.
Welsh, J.B. et al., "Analysis of Gene Expression Identifies Candidate Markers and Pharmacological Targets in Prostate Cancer" Cancer Res (2001) pp. 5974-5978, vol. 61.
Kunjo, LP et al., "Prostate-specific antigen, high-molecular-weight cytokeratin (clone 34betaE12), and/or p63: an optimal immunohistochemical panel to distinguish poorly differentiated prostate adenocarcinoma from urothelial carcinoma" Am J Clin Pathol (May 2006) pp. 675-681, vol. 125, No. 5.
Park, K. et al., "Application of ERG/TFF3/HMWCK Triple Immunostain: A Novel Diagnostic Biomarker in Prostate Needle Biopsies" (Mar. 21, 2012) Annual Meeting, Poster Session VI #169.
International Search Report dated Sep. 12, 2013 issued in International Application No. PCT/US2013/041155.

* cited by examiner

*Primary Examiner* — Lisa Cook
(74) *Attorney, Agent, or Firm* — Scully, Scott, Murphy & Presser, P.C.

(57) ABSTRACT

This invention relates to a triple immunostaining assay (ERG/TFF3/HMWCK) for sensitive and specific detection of prostate cancer. Positive staining for at least one of ERG or TFF3 combined with negative staining of HMWCK in a sample such as prostate tissue sample is indicative of cancer.

17 Claims, 6 Drawing Sheets
(6 of 6 Drawing Sheet(s) Filed in Color)

ERG/TFF3/HMWCK TRIPLE IMMUNOSTAIN FOR DETECTION OF PROSTATE CANCER

CROSS REFERENCE TO RELATED APPLICATION

This application claims priority from U.S. Provisional Application No. 61/647,076, filed May 15, 2012, the entire contents of which are incorporated herein by reference.

STATEMENT REGARDING FEDERALLY SPONSORED RESEARCH OR DEVELOPMENT

This invention was made with Government Support under the following grants: the NCI Early Detection Research Network 5U01 CA11275-07, I4-A424, and DOD Synergy W81XWH-11-1-0410. The Government has certain rights in this invention.

FIELD OF THE DISCLOSURE

This invention relates to detection and characterization of prostate cancer. In particular, this invention relates to a triple immunostaining assay (ERG/TFF3/HMWCK) for sensitive and specific detection of prostate cancer.

BACKGROUND ART

Prostate cancer is a molecularly heterogeneous disease with recently characterized cancer-specific gene aberrations (Lapointe J. et al., *Cancer Research* 67:8504-8510 (2007); Demichelis F. et al., *Genes Chromosomes Cancer* 48:366-380 (2009); Berger M F et al., *Nature* 470:214-220 (2011)). The most common genetic alteration found in prostate cancer is TMPRSS2-ERG gene fusion, which occurs in approximately 50% of cases (Kumar-Sinha C. et al., *Nat Rev Cancer* 8:497-511 (2008); Mosquera J M et al., *Clin Cancer Res* 15:4706-4711 (2009); Tomlins S A et al., *Eur Urol* 56:275-286 (2009); Tomlins S A et al., *Science* 310:644-648 (2005)). ERG over-expression due to the androgen-regulated TMPRSS2 gene is a proxy for the gene fusion and serves as a prostate cancer-specific biomarker (Park K. et al., *Neoplasia* 12:590-598 (2010)). The detection of over-expressed cancer-associated genes from expression profiling analyses has introduced novel potential biomarkers (Tomlins S A et al., *Cancer Cell* 13:519-528 (2008); Luo J. et al., *Cancer Res* 61:4683-4688 (2001); Qian D Z et al., *Clin Cancer Res* 15:3135-3142 (2009); Magee J A et al., *Cancer Res* 61:5692-5696 (2001); Welsh J B et al., *Cancer Res* 61:5974-5978 (2001)). TFF3 is one of the three members of the TFF gene family located near TMPRSS2 on chromosome 21q22.3. Besides their prominent expression in mucous epithelia, these peptides are also synthesized in the central nervous system (Jagla W. et al., *FASEB J* 14:1126-1131 (2000)). It has been reported that TFF3, over-expressed in about 50% of prostate cancers and inhibited by concurrent ERG expression and AR signaling (Rickman D S et al., *Neoplasia* 12:1031-1040 (2010); Faith D A et al., *Prostate* 61:215-227 (2004); Garaway I P et al., *Prostate* 61:209-214 (2004)), is also involved in regulation of cell migration, invasion, and angiogenesis in other cancers.

SUMMARY OF THE DISCLOSURE

This disclosure is directed to a triple immunohistochemistry (IHC) assay and related reagents for detecting TFF3, ERG, and high-molecular weight cytokeratins (HMWCK) as basis for diagnosing prostate cancer. It has been demonstrated herein that this triple immunostain provides a sensitive and specific in situ detection of prostate cancer. ERG protein expression was present in 45% of prostate cancers and TFF3 was overexpressed in 36%, significantly more in ERG-negative than ERG-positive tumors. The feasibility of this triple immunostain has also been demonstrated in needle biopsies.

In one aspect, this disclosure provides an immunohistochemistry (IHC) assay for in situ detection of TFF3, ERG, and high-molecular weight cytokeratins (HMWCK). In certain embodiments, the assay is performed on samples containing cells of the prostate tissue, including tissue samples and needle biopsy samples, from a subject. In some embodiments, the three markers are stained sequentially. In specific embodiments, the markers are stained in the order of ERG, TFF3 and HMWCK. In other embodiments, the three markers or at least two of the three markers are stained simultaneously.

In a further aspect, the disclosure provides a method of detecting prostate cancer based on the triple immunostaining assay described herein. Positive staining for at least one of ERG or TFF3 in a sample combined with negative staining of HMWCK is indicative of cancer.

In another aspect, the disclosure provides a kit containing reagents for performing the triple immunostaining assay described herein. The kit generally includes antibodies directed to ERG, TFF3 and HMWCK proteins and other appropriate reagents to permit generation of detectable colors for the three markers (e.g., three distinct colors). The kit may additionally include instructions on how the assay is performed.

BRIEF DESCRIPTION OF THE DRAWINGS

The patent or application file contains at least one drawing executed in color. Copies of this paper or patent application publication with color drawing(s) will be provided by the Office upon request and payment of the necessary fee.

FIG. 2. HGPIN demonstrates similar immunoprofile to adjacent prostate cancer. A) ERG-positive HGPIN and adjacent cancer glands with same biomarker expression. Note that tumor glands with perineural invasion (right-upper corner) have ERG/TFF3 co-expression. B) TFF3-positive HGPIN and adjacent cancer glands with identical biomarker expression. HMWCK expression highlights the basal cells of benign glands and HGPIN. (H&E stain in panels on left; ERG/TFF3/HMWCK triple immunostain in panels on right.)

FIG. 4. Heterogeneous ERG and TFF3 expression in prostate cancer. A) Two separate foci (arrowhead and asterisk) of prostatic adenocarcinoma Gleason score 3+3=6 and multiple HGPIN lesions are seen on H&E. B) Distinct areas are noted with ERG/TFF3/HWMCK triple immunostain: ERG-positive prostate cancer adjacent to ERG-positive HGPIN (arrowhead), TFF3-positive prostate cancer adjacent to TFF3-positive HGPIN (asterisk), and ERG/TFF3-positive HGPIN (arrow). C) ERG-positive tumor demonstrates ERG translocation through insertion by FISH break-apart assay (inset). D) ERG/TFF3-positive HGPIN demonstrates ERG translocation through insertion by FISH break-apart assay (inset). E) TFF3-positive tumor demonstrates no ERG translocation by FISH break-apart assay (inset).

FIG. 6. Potential application of ERG/TFF3/HMWCK triple immunostain in prostate needle biopsies. Strong expression of ERG or TFF3 (mid panel) in atypical glands suspicious for carcinoma compared to H&E (left panel) and p63/HMWCK stain (right panel). A) ERG-positive atypical gland suspicious for carcinoma (arrowhead) close to ERG-positive HGPINs. Arrow indicates outpouching of HGPIN. B) TFF3-positive atypical gland suspicious for carcinoma and adjacent TFF3-positive HGPIN. HMWCK expression is observed in the basal cells of benign glands and HGPIN, and ERG expression in endothelial cells serves as internal control. (H&E stain in panels on left; ERG/TFF3/HMWCK triple immunostain in mid panels; p63 and HMWCK stain in panels on right, 40x.)

DETAILED DESCRIPTION

Triple Stain

One aspect of this invention is directed to a triple strain immunohistochemistry (IHC) assay for the detection of three markers, TFF3, ERG, and high-molecular weight cytokeratins (HMWCK), in a tissue sample and simultaneous observation of three signals (e.g., in one slide).

Sample Source and Preparation

In accordance with this disclosure, the triple stain assay is performed on samples containing cells of the prostate tissue from a subject, such as a human or other mammalian subject. Examples of suitable samples include prostate biopsies, prostatectomy tissues, and prostate cell samples which can be collected, for example, by prostate massage, in the urine, or in need biopsy (such as fine needle aspirates).

Both freshly collected samples and processed samples (e.g., frozen post-collection) can be used in the triple stain assay of this invention. In some embodiments, the cells are fixed using a fixative agent to preserve cell morphology and tissue architecture. Suitable fixative agents are well known in the art and include 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative. In certain embodiments, the cells are fixed using formalin and/or wax (e.g., paraffin).

In certain embodiments, thin sections of about 4-40 µm thick are sliced from the tissue by using, e.g., a microtome. Alternatively, the whole tissue retrieved can be used directly without slicing. The slices or whole tissue specimens are mounted on a solid support that permits convenient detection. Exemplary supports include microscope slides (e.g., glass or plastic microscope slides), coverslips (e.g., glass or plastic coverslips), tissue culture dishes, multi-well plates, membranes (e.g., nitrocellulose or polyvinylidene fluoride (PVDF)) or chips.

The sample may be additionally treated in order to make epitopes available for antibody binding, including, e.g., deparaffinization and antigen retrieval. In specific embodiments, the sample is treated for antigen retrieval (i.e., make epitopes available for antibody binding) through heat, e.g., heat treatment using microwave or incubation bath or chamber. In one embodiment, antigen retrieval for each of ERG, TFF3 and HMWCK can be accomplished using a citrate or EDTA-based solution (such as the Bond Epitope Retrieval Solutions, Leica Microsystems, Bannockburn, Ill.) at 99 to 100° C. for 20 minutes.

The samples may also be treated, for example, with a blocking reagent, to reduce background staining as a result of non-specific binding, the presence of endogenous biotin or enzymes (such as endogenous peroxidase). Examples of blocking reagents suitable for use herein include normal serum, non-fat dry milk, bovine serum albumin, gelatin, and other commercially available blocking buffers, which serve to block reactive (i.e., non-specific) sites to which the primary or secondary antibodies may otherwise bind.

Antibodies and Labeling Reagents

Depending upon the detection format (further described herein below), primary antibodies and secondary binding reagents (e.g., reagents containing secondary antibodies) can be utilized. Both primary and secondary antibodies can be either polyclonal or monoclonal. Primary antibodies as used herein refer to antibodies raised against an antigen of interest, i.e., TFF3, ERG, and HMWCK. Depending on the detection format, primary antibodies may be labeled or unlabelled. Secondary binding reagents bind to primary antibodies and can include antibodies, antigen-binding fragments or derivatives thereof (such as Fab, Fab', F(ab)2, Fd, Fd' or Fv fragments). Such antibodies in the secondary binding reagents can bind to immunoglobulins of the primary antibody species directly, or indirectly through an intermediate or linker antibody or antibody fragment or derivative. Secondary binding reagents can be conjugated or labeled with a reporter molecule, either directly or indirectly through a linker molecule, such as biotin (which can recruit avidin, strepavidin or neutravidin-linked reporter molecules), or a polymer (such as those provided in Bond Polymer Refine Red Detection System, which has the advantage of avoiding non-specific staining as a result of endogenous biotin).

Primary antibodies suitable for use herein for detection of ERG should be directed to the C-terminus of the ERG protein. ETS gene rearrangements have been confirmed to exist in prostate cancer, with TMPRSS2-ERG gene fusion being the most common variant. Almost all reported TMPRSS2-ERG transcript isoforms encode a truncated ERG. Human ERG protein is composed of 486 amino acids, and is characterized by a pointed domain (amino acids 115-197), and the ETS domain (amino acids 310-393), among other structural features. In some embodiments, antibodies to ERG suitable for use in this invention are directed to, i.e., binds to, the C-terminal portion of human ERG protein containing amino acids 310-486, 350-486, or 390-486. In specific embodiments, an ERG antibody is directed to a C-terminal portion of human ERG containing amino acids 393-479, which are retained in all known ERG gene fusion isoforms. An example of a suitable ERG antibody is monoclonal antibody EPR 3864, available from Ventana Medical Systems, Inc., Tucson, Ariz., or an antibody which binds to or competes for binding to the same epitope as antibody 3864.

Primary antibodies suitable for use herein for detection of TFF3 are also available and/or can be readily generated. TFF is a member of a family of polypeptides characterized by having at least one copy of the trefoil motif, a 3-leaved structure formed by three conserved disulfides within a 40-amino acid segment. Human TFF3 is composed of 73 amino acids, with amino acids 24-65 constituting the trefoil domain. In some embodiments, antibodies to TFF3 suitable for use in this invention are directed to an N-terminal portion of human TFF3, for example, an N-terminal portion containing amino acids 1-45, amino acids 1-35, or amino acids 1-25. In other embodiments, a suitable TFF3 antibody binds to a C-terminal portion of human TFF3. An example of a suitable TFF3 antibody is monoclonal antibody 15C6, available from EMD Chemicals, Inc., Gibbdtown, N.J., or an antibody which binds to or competes for binding to the same epitope as antibody 15C6.

Primary antibodies suitable for use herein for detection of HMWCK are also available and/or can be readily generated. Cytokeratins are intermediate filaments present in all epithelial cells, and a number of non-epithelial cells. There are two types of cytokeratins: type I, the acidic type, assigned Moll Nos. 10-20; and type II, the basic or neutral type, assigned Moll No. 1-9. The cytokeratins can also be divided into low molecular weight cytokeratins (commonly CK8, CK18 and CK19), and high molecular weight cytokeratins ("HMWCK") (commonly CK1, CK5, CK10 and CK14, having molecular weight of 66, 57, 51 and 49 kD, respectively). In some embodiments, a suitable primary antibody is directed to one high molecular weight cytokeratin, i.e., one of CK1, CK5, CK10 and CK14. In other embodiments, a suitable primary antibody binds to multiple high molecular weight cytokeratins, i.e., two or more of CK1, CK5, CK10 and CK14. An example of a suitable primary antibody which binds to multiple high molecular weight cytokeratins and serves as a marker of basal cells in prostate tissues is monoclonal antibody 34βE12 or 34 BE12, available from Dako, Carpinteria, Calif., or an antibody which binds to or competes for binding to the same epitope as antibody 15C6. This antibody has been shown to react with the 66, 57, 51 and 49 kD proteins corresponding to cytokeratins 1, 5, 10 and 14.

Depending on the detection format, primary antibodies or secondary binding reagents are labeled (i.e., conjugated or linked, directly or indirectly through a linker) to a reporter molecule which is capable of generating a detectable signal (e.g., a chromogenic or fluorescent signal). For chromogenic reporter systems, generally an antibody or agent is labeled (directly or indirectly) with an enzyme, which upon reacting with a chromogenic substrate, yields a colored pigment that can be analyzed with an ordinary light microscope. Commonly used enzymes include alkaline phosphatase (AP) and horseradish perodidase (HRP). An array of chromogenic, fluorogenic and chemiluminescent substrates is available for use with either enzyme. Examples of chromogens include diamineobenzidine (or "DAB", available from Leica Microsystems, Bannockburn, Ill.) (brown staining), Refine Red (Fast Red chromogen, available from Leica Microsystems), and Vector Blue (Vector Laboratories, Inc., Burlingame, Calif.). Examples of fluorescent reporters include small, organic molecules such as FITC, TRITC and AMCA, and their derivatives. Densitometric analysis of the signals can provide quantitative data, if desired.

In certain embodiments, the triple stain of this invention is designed to generate three distinct color pigments for the three markers. Two or all three of the colors, although distinct, can be merged to produce a fourth distinct color. In a specific embodiment, the triple stain assay is designed to stain nuclear ERG in a brown color (using DAB), cytoplasmic TFF3 in a red color (using, e.g., the Refine Red reagent from Leica), and cytoplasmic HMWCK in a blue color (using, e.g., the Vector Blue reagent from Vector Lab).

Detection Formats

In some embodiments, detection of one or more of the three markers is performed in a direct IHC format where the primary antibody or antibodies for one or more of the markers are labeled directly or indirectly via a linker molecule with a reporter molecule.

In other embodiments, detection of one or more markers is performed in an indirect IHC format where the primary antibody or antibodies are unlabeled, but the secondary antibody or antibodies are labeled directly or indirectly via a linker molecule with a reporter molecule and bind to the primary antibody or antibodies directly or indirectly.

In specific embodiments, detection of each of the three markers utilizes an indirect IHC format. For example, an unlabeled primary antibody is applied to a sample in question. Subsequently a post primary antibody linker reagent is applied which binds to the primary antibody. Finally a further antibody is applied, which is conjugated with a reporter molecule (such as AP or HRP) or a polymeric reporter (e.g., polymeric HRP or polymeric AP as provided in the Bond Polymer Refine Detection and the Bond Polymer Refine Red Detection systems, respectively, from Leica Microsystems). In specific embodiments, ERG is stained using the Bond Polymer Refine Detection system; and both TFF3 and HMWCK are stained using the Bond Polymer Refine Red Detection system.

In some embodiments, the three markers are stained sequentially. In a sequential staining format, an IHC process is performed for a first marker, followed by an IHC process for a second marker, which is then followed by an IHC process for a third marker. Each IHC process may involve antigen retrieval, blocking (optional), contacting with a primary antibody, contacting with a secondary binding reagent when the primary antibody is unlabeled, and detecting the signals generated. In a specific embodiment, the markers are stained in the order of ERG, TFF3 and HMWCK. In another embodiment, the markers are stained in the order of TFF3, ERG and HMWCK.

In other embodiments, at least some of the steps for staining the three markers are combined in one single step. For example, primary antibodies for at least two of the three markers, or secondary antibodies for detecting at least two of the three markers are brought into contact with the sample simultaneously, e.g., in an antibody cocktail.

After immunohistochemical staining of the three target antigens, a further stain may be applied to provide contrast and enhance the effect of the primary stain. Many of such contrasting stains show specificity for discrete cellular compartments or antigens, while others stain the whole cell. Both chromogenic and fluorescent dyes are available as contrast stains, including hematoxylin (nuclear), Hoechst stain, DAPI, Nuclear Fast Red, Methyl Green, and Methyl Blue, among others.

The images of the triple stain assay can be evaluated manually, e.g., by a pathologist, or by an automated device. Quantitative or semi-quantitative evaluation can be achieved by examining cells in a number of areas within a tissue section. Cells are determined to stain positive or negative for a marker based on the intensity of the staining and a manually or arbitrarily determined threshold. In specific embodiments, only staining having moderate-strong intensity is considered positive for TFF3; and staining of any intensity is considered positive for ERG.

Diagnosis of Prostate Cancer

In a further aspect, the disclosure provides a method of detecting prostate cancer based on the triple immunostaining assay described herein.

In accordance with this disclosure, positive staining for at least one of ERG or TFF3 in a prostate tissue sample is indicative of cancer, except when HMWCK also stains positive indicative of benign basal cells. That is, cells displaying positive staining of at least one of ERG or TFF3 in conjunction with negative staining for HMWCK are identified as cancerous cells.

The triple stain assay of this invention has been shown to provide sensitive and specific detection of prostate cancer using both prostatectomy tissue specimens and needle biopsy samples. The advantages of the triple stain disclosed herein include the high specificity of ERG expression in prostate cancer, and the overall inverse relationship of ERG and TFF3 expression, complemented by the HMWCK staining which, inter alia, differentiates between HGPIN and tumor glands in the presence of ERG or TFF3 expression. The present assay will provide values in both diagnosing prostate cancer, and also monitoring treatment efficacies.

Triple Stain Kits

In a further aspect, the disclosure provides a kit containing reagents for performing the triple immunostaining assay described herein. The kit generally includes primary antibodies directed to ERG, TFF3 and HMWCK proteins, optionally secondary antibodies with labels, and other appropriate reagents to permit generation of detectable signals for each of the three markers (e.g., three distinct colors). The kit may additionally include instructions on how the assay is performed.

The present description is further illustrated by the following examples, which should not be construed as limiting in any way. The contents of all cited references (including literature references, issued patents, and published patent applications as cited throughout this application) are hereby expressly incorporated by reference.

EXAMPLE 1

Materials and Methods

Development of ERG/TFF3/HMWCK Triple Stain and IHC Evaluation

ERG/TFF3/HMWCK triple IHC staining was accomplished by sequentially applying the three antibodies using Bond Max autostainer (Leica Microsystems, Bannockburn, Ill.). Heat induced antigen retrieval was performed to all three stains. Bond Polymer Refine Detection was used to stain ERG (clone EPR 3864, 1:175 from Ventana Medical Systems, Inc., Tucson, Ariz.), and Bond Polymer Refine Red Detection to stain both TFF3 (clone 15C6, 1:200 from EMD Chemicals, Inc., Gibbstown, N.J.) and HMWCK (clone 34BE12, 1:175 from Dako, Carpinteria, Calif.). Diaminobenzidine (DAB, Leica Microsystems), Refine Red (Leica Microsystems), and Vector Blue (Vector laboratories, Inc., Burlingame, Calif.) chromogens were used for ERG, TFF3, and HMWCK, respectively.

Study pathologists performed semi-quantitative evaluation of nuclear ERG (brown color) and cytoplasmic TFF3 (red color) expression using a four-tier grading system: negative (0), weakly positive (1+), moderately positive (2+), and strongly positive (3+). Any staining was considered positive for ERG expression. For TFF3, moderate and strong intensities (2+ and 3+) were considered a positive result.

ERG/TFF3/HMWCK Triple Stain Validation and Testing

Tissue microarrays (TMAs) were constructed using formalin-fixed paraffin-embedded (PIPE) tissue from prostatectomy specimens of 96 men who underwent radical prostatectomy at our institution, as a monotherapy for clinically localized prostate cancer. The dominant and secondary tumor nodules available from each prostatectomy specimen were represented in the TMAs. The latter also included benign tissue of 52 cases. The clinical demographics of this cohort are presented in Table 1.

TABLE 1

Clinical Demographics of the Prostate Cancer Cohort (n = 96)

| Age: | |
|---|---|
| Max Age | 75 |
| Min Age | 42 |
| Median | 62 |
| PSA: | |
| Max PSA | 24.23 |
| Min PSA | 1.9 |
| Median PSA | 5.1 |
| PSA < 10 | 83 |
| PSA = 10-20 | 10 |
| PSA > 20 | 3 |
| Gleason Score: | |
| <7 | 12 |
| =7 | 71 |
| >7 | 13 |
| Tumour stage: | |
| pT2 | 62 |
| pT3 | 32 |
| pT4 | 2 |
| Surgical margin: | |
| Negative | 80 |
| Positive | 16 |
| PSA Biochemical recurrence*: | |
| No | 86 |
| Yes | 9 |

*Clinical follow-up of one patient was not available.
Abbreviations: Max = Maximum; Min = Minimum; PSA = Prostate Specific Antigen.

After validation of ERG/TFF3/HWMCK prostate triple stain on TMAs, 76 prostate needle biopsies were also subjected to IHC and evaluated by study pathologists. Forty-one of these biopsies contained different amounts of prostatic adenocarcinoma with Gleason score 3+3=6 (n=38) and 3+4=7 (n=3), and high-grade prostatic intraepithelial neoplasia (HGPIN). The other 35 biopsies contained atypical glands suspicious for prostate cancer and HGPIN.

Chromogranin A IHC in Benign Cases

To highlight the neuroendocrine origin of strong TFF3-expressing cells in the non-luminal layer of benign cases (Faith D A et al., *Prostate* 61:215-227 (2004)), TMAs were stained with Chromogranin A antibody (LK2H10, 1:400; Biogenex, San Ramon, Calif.) using Bond Max autostainer.

Assessment of ERG Gene Rearrangement by Fluorescence In Situ Hybridization (FISH)

Four micrometer-thick tissue sections were used to perform dual-color break-apart interphase FISH assay as previously described (Tomlins S A et al., *Science* 310:644-648 (2005); Perner S. et al., *Cancer Res* 66:8337-8341 (2006)). Briefly, ERG gene rearrangement status was assessed using centromeric (BAC clone RP11-24A11 labeled green) and telomeric (BAC clone RP11-372017 labeled red) probes, and determined independently by the study pathologists. Detection of two pairs of juxtaposed red and green signals that usually form two yellow signals demonstrates absence of ERG rearrangement. A nucleus with ERG rearrangement through insertion shows one yellow signal for the normal allele and break up of green-red signals for the rearranged allele. Rearrangement through deletion demonstrates a yellow combined signal and a single red signal for the rearranged allele. Benign epithelial and stromal cells have two yellow signals per nucleus and serve as internal controls for this break-apart FISH assay.

Statistical Analysis

Chi-square test and Fisher's exact test was used to evaluate association between categorical variables. One-way ANOVA was performed to compare continuous variables (e.g. age) among groups (e.g. TFF3/ERG). For all statistical tests, a P-value <0.05 was considered statistically significant.

EXAMPLE 2

Results

ERG and TFF3 Protein Expression in Prostate Cancer

Figure 1:
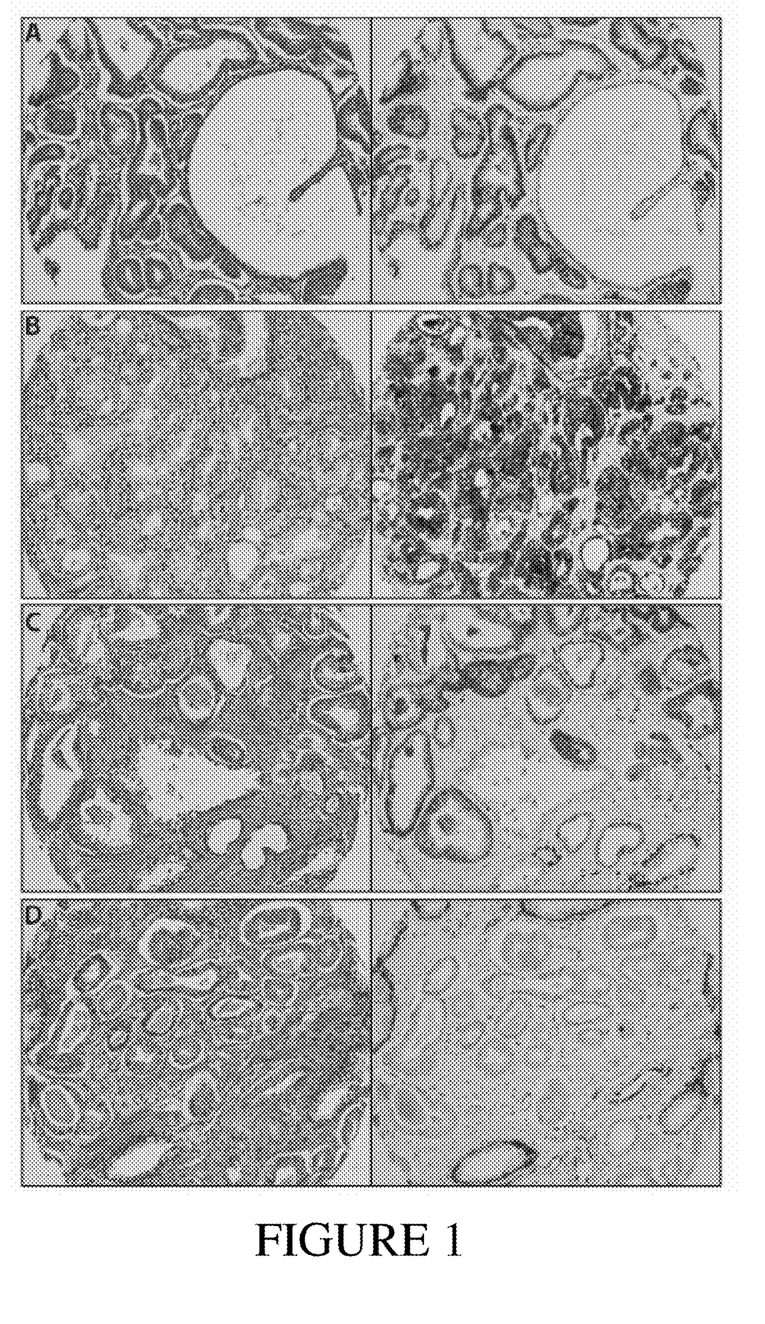
FIG. 1. Validation of ERG/TFF3/HMWCK triple immunostain for the detection of prostate cancer using tissue microarrays (TMAs). Four cases of prostatic adenocarcinoma with different immunoprofiles are illustrated. ERG (nuclear), TFF3 (cytoplasmic), and HMWCK (cytoplasmic) expression is highlighted by Diaminobenzidine (brown), Refine Red (red), and Vector Blue (blue) chromogens, respectively. A) ERG-positive prostate cancer. B) TFF3-positive prostate cancer. The mutually exclusive expression of ERG and TFF3 is seen in these first two panels. C) Prostatic adenocarcinoma with ERG/TFF3 co-expression. D) Prostatic adenocarcinoma negative for both ERG and TFF3. HMWCK expression is observed in the basal cells of benign glands and HGPIN. ERG nuclear expression is present in endothelial cells, which serves as internal control. (H&E stain in panels on left; ERG/TFF3/HMWCK triple immunostain in panels on right.)

Of the 96 tumor cases, 45% (43/96) and 36% (35/96) showed ERG and TFF3 over-expression, respectively. 5% (5/96) demonstrated co-expression and 24% (23/96) had neither ERG nor TFF3 expression (FIG. 1). An inverse relationship between ERG and TFF3 expression was confirmed with 57% (30/53) of ERG-negative tumors expressing TFF3 compared to 12% (5/43) of ERG-positive tumors (Chi-Square test, p<0.0001).

ERG/TFF3 Staining Pattern in Prostate Cancer

Figure 2:
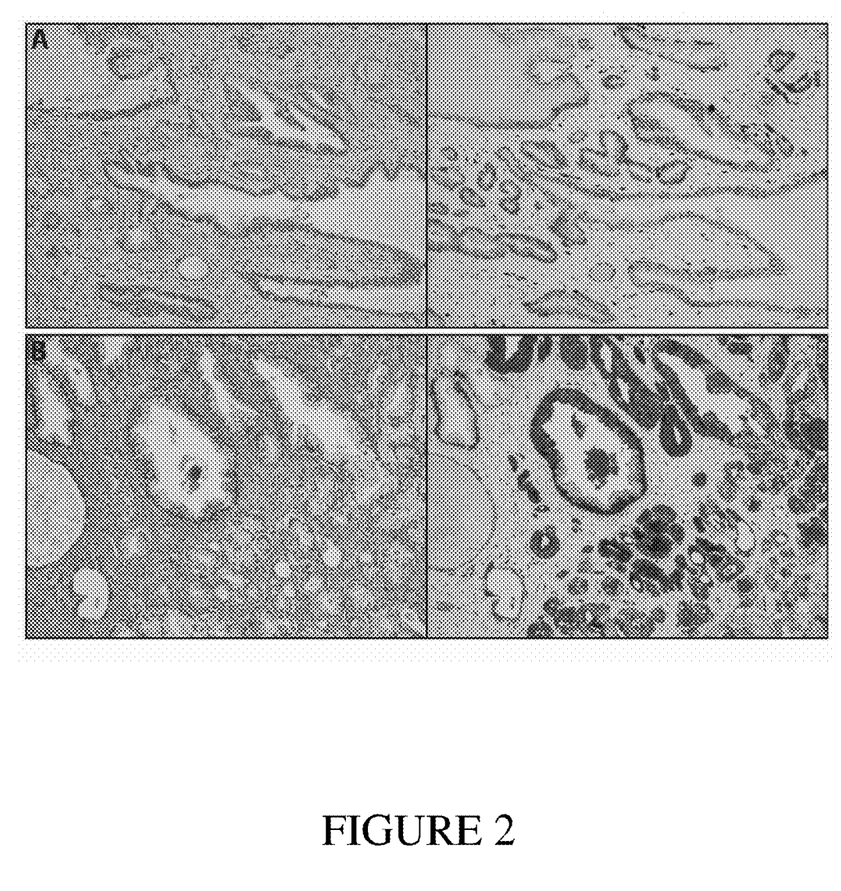

In regard to intensity, ERG IHC demonstrated homogenous nuclear staining in ERG-positive cases (FIG. 1). Based on the staining pattern of different cores taken from a given tumor nodule, the extent of ERG staining was homogenous as well. Strong ERG nuclear expression in endothelial cells served as internal control, and weak to moderate nuclear staining was also seen in lymphocytes. TFF3 IHC revealed a heterogeneous staining pattern in terms of both intensity and percentage of positive cells within a tumor nodule. Similar to ERG, TFF3 expression was documented in isolated high-grade prostatic intraepithelial neoplasia (HGPIN), as well as in HGPIN adjacent to positive tumor glands (FIG. 2). When present in prostate biopsies, TFF3 had moderate to strong cytoplasmic expression in colonic mucosa, serving as internal control (not shown).

ERG/TFF3 Staining Pattern in Benign Tissues

Figure 3:
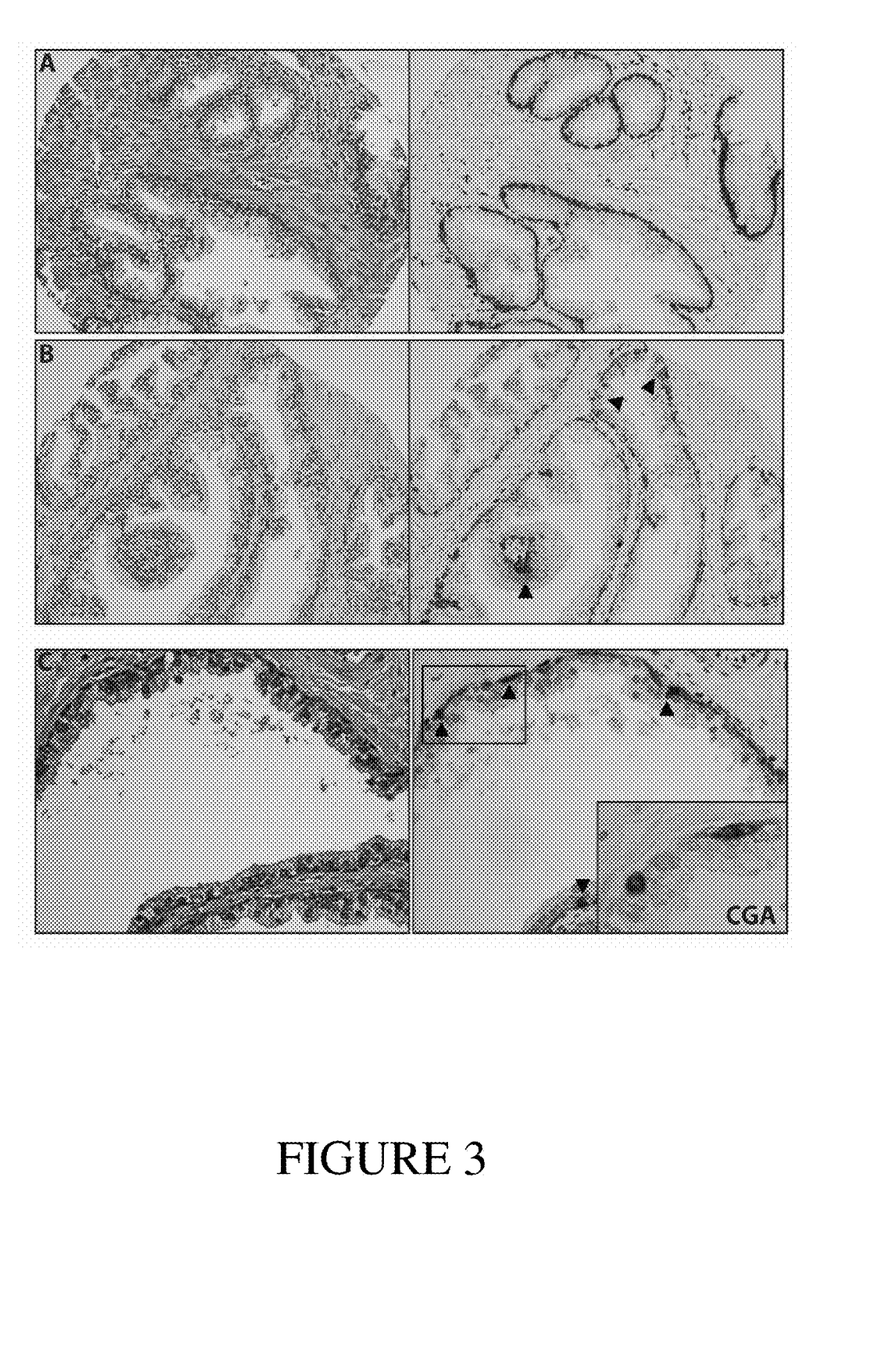
FIG. 3. TFF3 expression in benign glands. A) TFF3-negative benign glands. B) Focally TFF3-positive benign glands. Weak and focal TFF3 expression in luminal epithelial cells (arrowheads) is noted. C) Focally TFF3-positive benign gland. Rare cells (arrowheads) demonstrate strong TFF3 positivity. These correspond to scattered neuroendocrine cells in benign glands, highlighted by chromogranin A (CGA) immunostain (inset). (H&E stain in panels on left; ERG/TFF3/HMWCK triple immunostain in panels on right.)

No ERG expression was observed in benign prostate tissue. Mostly weak-focal TFF3 staining in luminal epithelial cells was present in 44% (23/52) of benign cases, only two of which had moderate-focal intensity and were considered TFF3-positive (Table 2 and FIG. 3). Occasional benign cases demonstrated strong-focal TFF3 positivity towards the basal cell layer. These cells were also positive for Chromogranin A, confirming the presence of scattered neuroendocrine cells in benign glands (FIG. 3C). TFF3 intensity correlated significantly with type of tissue (p=0.0001, Chi-square test). Specifically, 53% (35/66 cases) of TFF3-positive tumor cases had moderate or strong intensity, but only 4% of benign cases (2/52) had moderate-focal expression of the protein.

ERG Protein Expression Correlates with ERG Gene Rearrangement Status

All cases represented in TMAs as well as in prostate biopsies were interrogated for ERG gene rearrangement by FISH. There was 100% concordance between ERG expression by IHC and ERG gene status by FISH.

Molecular Heterogeneity in Prostate Cancer

Figure 4:
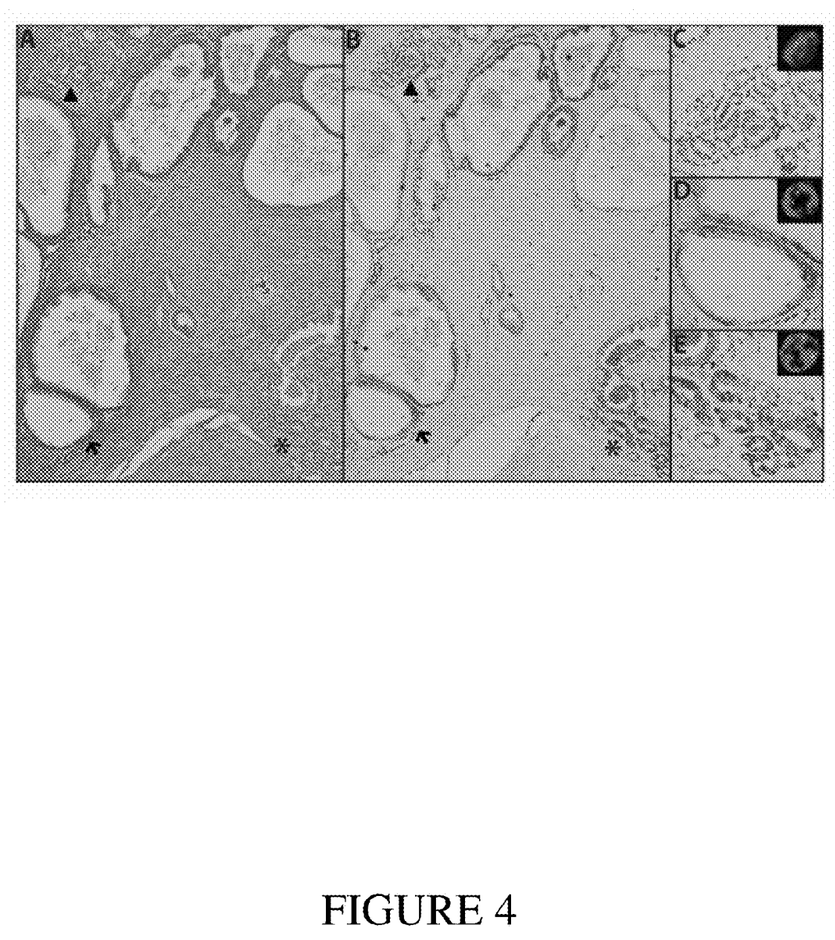

Differential expression of ERG and TFF3 underscores the complexity and diversity of molecular events occurring in discrete tumors arising in the prostate of the same individual. FIG. 4 illustrates the results of triple immunostain and ERG break-apart FISH assay in a full section of a prostatectomy case with two separate tumor foci. This particular case was reassessed given an initial discrepancy of results in IHC performed on TMA. Although the Gleason grade is identical and the histomorphology is very similar in two tumor foci, these correspond to two distinct prostate cancers based on their differential expression profiles detected by ERG/TFF3/HMWCK IHC and different ERG fusion status detected by FISH.

Translational Utility and Validation of the Assay

Figure 5:
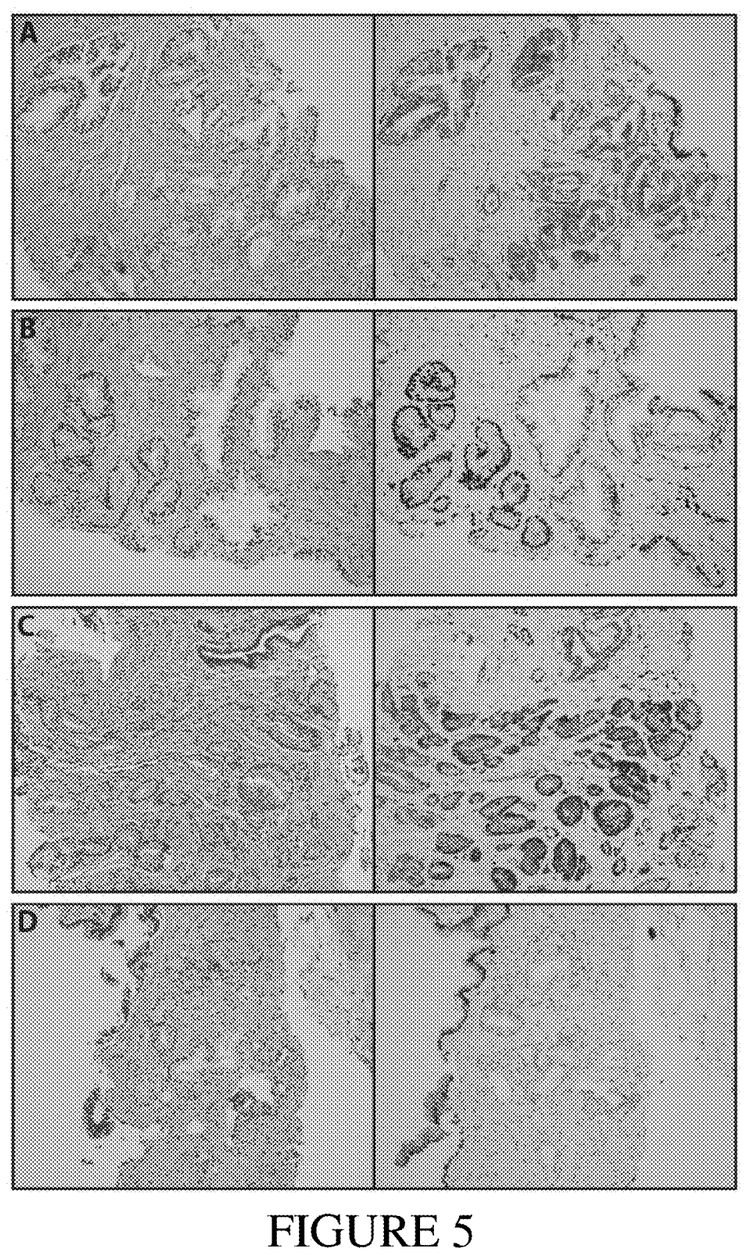
FIG. 5. Feasibility of ERG/TFF3/HMWCK triple immunostain in prostate needle biopsies. A) TFF3-positive prostate cancer and adjacent TFF3-positive HGPIN. B) ERG-positive prostate cancer close to ERG-positive HGPIN. C) ERG/TFF3-positive prostatic adenocarcinoma. D) One of the cases of prostatic adenocarcinoma that was negative for ERG or TFF3 expression. HMWCK expression is observed in the basal cells of benign glands and HGPIN, and ERG expression in endothelial cells serves as internal control. (H&E stain in panels on left; ERG/TFF3/HMWCK triple immunostain in panels on right.)
Figure 6:
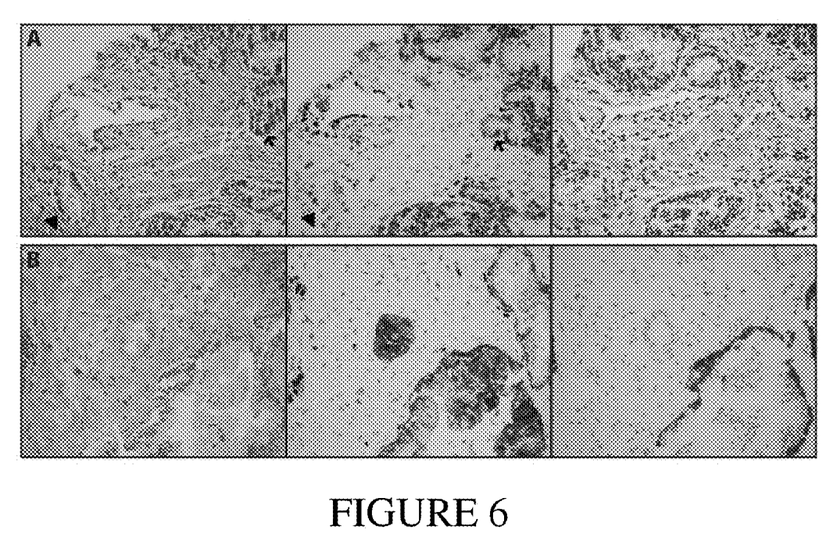

Based on the TMA data, the sensitivity and specificity of ERG and TFF3 in staining prostate cancer were shown herein to be 76% and 96%, respectively. HMWCK expression in the cytoplasm of basal cells (blue chromogen) facilitated in the differentiation between HGPIN and tumor glands in the presence of ERG or TFF3 expression (FIG. 2). To further evaluate the potential use of the ERG/TFF3/HMWCK triple stain, the IHC protocol was applied to 76 prostate biopsies containing different extents of prostatic adenocarcinoma, HGPIN, and atypical glands suspicious for cancer (see Materials and Methods). Robust reproducibility was seen in this set of biopsies (FIG. 5). Among prostate biopsies containing cancer (n=41), tumor areas were highlighted in 78% (32/41) of them either by positive staining for ERG only (n=19), TFF3 only (n=12), or co-expression of ERG and TFF3 (n=1), along with absence of basal cells (negative staining for HMWCK). Nine tumors were negative for either biomarker. 46% (16/35) of foci of atypical glands suspicious for carcinoma present in the remainder of the biopsies were highlighted by positive staining for ERG only (n=5) or TFF3 only (n=11), accompanied by absence of basal cells. Nineteen (54%) of these cases were negative for either biomarker.

Correlation with Clinical-Pathological Parameters

No associations between ERG/TFF3 expression in tumors (n=96) and clinical or pathologic parameters (i.e. age, PSA, Gleason score, tumor stage, and biochemical recurrence) were observed.

TABLE 2

Intensity of TFF3 Protein Expression in Tumor and Benign Glands on TMAs

| Intensity | Benign | Tumor |
|---|---|---|
| Negative (0) | 29 | 30 |
| Weak (1+) | 21 | 31 |
| Moderate-Strong (2+ and 3+) | 2 | 35 |
| Total | 52 | 96 |

TABLE 3

ERG/TFF3/HMWCK Immunostain on Prostate Needle Biopsies (n = 76)

| | PCA | Atypical glands suspicious for carcinoma |
|---|---|---|
| ERG+/TFF3− | 19 (46.3%) | 5 (14.3%) |
| ERG−/TFF3+ | 12 (29.3%) | 11 (31.4%) |
| ERG+/TFF3+ | 1 (2.4%) | 0 (0%) |
| ERG−/TFF3− | 9 (22%) | 19 (54.3%) |
| Total | 41* | 35 |

*Three out of 41 PCA cases were Gleason grade 7 (3 + 4). Two were ERG+/TFF3−, and one was negative for both ERG and TFF3.

What is claimed is:

1. A triple immunohistochemistry (IHC) assay for in situ detection of TFF3, ERG, and a high-molecular weight cytokeratin (HMWCK), comprising:
   providing a prostate tissue sample comprising fixed cells;
   contacting the sample with a first primary antibody directed to a first molecule selected from ERG, TFF3 or HMWCK, a second primary antibody directed to a second molecule selected from ERG, TFF3 or HMWCK, and a third primary antibody directed to a third molecule selected from ERG, TFF3 or HMWCK, to permit formation of antibody-antigen complexes in the sample which lead to the generation of detectable signals; and
   identifying cells that display a detectable signal.

2. The triple IHC assay of claim 1, further comprising contacting the sample with a first secondary binding reagent which binds to said first primary antibody and is labeled with a first reporter molecule, contacting the sample with a second secondary binding reagent which binds to said second primary antibody and is labeled with a second reporter molecule, and contacting the sample with a third secondary binding reagent which binds to said third primary antibody and is labeled with a third reporter molecule, wherein said first, second and third reporter molecules are capable of generating detectable signals.

3. The triple IHC assay of claim 2, wherein said first, second and third reporter molecules generate three distinct signals.

4. The triple IHC assay of claim 2, wherein said first, second and third reporter molecules each comprise an enzyme that acts on a chromogenic substrate to form a pigment.

5. The triple IHC assay of claim 4, wherein said first, second and third reporter molecules form three distinct pigments.

6. The triple IHC assay of claim 5, wherein said three distinct pigments are brown, red and blue in color.

7. The triple IHC assay of claim 2, wherein the sample is contacted with said first primary antibody, followed by said first secondary binding reagent; then with said second primary antibody, followed by said second secondary binding reagent; and subsequently with said third primary antibody, followed by said third secondary binding reagent.

8. The triple IHC assay of claim 7, wherein the first primary antibody is directed to ERG, the second primary antibody is directed to TFF3, and the third primary antibody is directed to a HMWCK.

9. The triple IHC assay of claim 8, wherein the secondary binding reagents generate pigments of brown, red and blue colors for ERG, TFF3 and HMWCK, respectively.

10. The triple IHC assay of claim 1, wherein cells displaying signals for at least one of ERG or TFF3 and lacking a signal for HMWCK are identified as cancerous cells.

11. The triple IHC assay of claim 1, wherein said tissue sample is a needle biopsy sample.

12. A method of detecting prostate cancer in a subject, comprising
   obtaining a prostate tissue sample comprising fixed cells from the subject;
   contacting the sample with a first primary antibody directed to a first molecule selected from ERG, TFF3 or HMWCK, a second primary antibody directed to a second molecule selected from ERG, TFF3 or HMWCK, and a third primary antibody directed to a third molecule selected from ERG, TFF3 or HMWCK, to permit formation of antibody-antigen complexes in the sample which leads to the generation of detectable signals; and
   identifying cells that display a detectable signal; and
   determining cells as cancerous cells based on the presence of signals for at least one of ERG or TFF3 and the absence of signals for HMWCK.

13. A kit for performing a triple IHC assay, comprising antibodies directed to ERG, TFF3 and HMWCK, respectively.

14. The kit of claim 13, further comprising three secondary binding agents which bind to the primary antibodies directed to ERG, TFF3 and HMWCK, respectively, and are labeled each with a reporter molecule capable of generating a detectable signal.

15. The kit of claim 14, wherein the reporter molecules generate three distinct signals.

16. The kit of claim 15, wherein the reporter molecules each comprise an enzyme that acts on a chromogenic substrate to form a pigment, and the reporter molecules form three distinct pigments.

17. The kit of claim 16, wherein the three distinct pigments are brown, red and blue colors.

* * * * *

UNITED STATES PATENT AND TRADEMARK OFFICE
CERTIFICATE OF CORRECTION

| | | |
|---|---|---|
| PATENT NO. | : 9,678,077 B2 | Page 1 of 1 |
| APPLICATION NO. | : 14/401184 | |
| DATED | : June 13, 2017 | |
| INVENTOR(S) | : Mark A. Rubin et al. | |

It is certified that error appears in the above-identified patent and that said Letters Patent is hereby corrected as shown below:

In the Specification

Column 1, Line 11 Should Read:

STATEMENT REGARDING FEDERALLY SPONSORED RESEARCH OR DEVELOPMENT
This invention was made with Government Support under grant number CA011275 awarded by the National Institutes of Health and grant number W81XWH-11-1-0410 awarded by the Army/MRMC. The government has certain rights in the invention.

Signed and Sealed this
Fifth Day of September, 2017

Joseph Matal
*Performing the Functions and Duties of the
Under Secretary of Commerce for Intellectual Property and
Director of the United States Patent and Trademark Office*